United States Patent [19]
Bertolini

[11] Patent Number: 4,794,103
[45] Date of Patent: Dec. 27, 1988

[54] PHARMACEUTICAL COMPOSITIONS CONTAINING PEPTIDES OF THE CHOLECYSTOKININ-CERULEIN GROUP FOR THE THERAPY OF SHOCK CONDITIONS AND OF RESPIRATORY AND CARDIOCIRCULATORY INSUFFICIENCIES

[76] Inventor: Alfio Bertolini, 8, Vittorio Veneto Street, Scandiano (Reggio Emilia), Italy

[21] Appl. No.: 184

[22] Filed: Jan. 2, 1987

[30] Foreign Application Priority Data

Jan. 10, 1986 [IT] Italy .................. 19055 A/86

[51] Int. Cl.$^4$ .............................. A61K 37/02
[52] U.S. Cl. ........................ 514/12; 514/13; 514/14; 514/15; 514/16
[58] Field of Search ............... 530/324, 325, 326, 327, 530/328, 309; 514/12, 13, 14, 15, 16

[56] References Cited

U.S. PATENT DOCUMENTS 3,723,406  3/1973  Ondetti et al. ............... 530/327
3,931,141  1/1976  Wissmann et al. ............ 530/309

FOREIGN PATENT DOCUMENTS 3138233  4/1983  Fed. Rep. of Germany .

OTHER PUBLICATIONS

Handbook of Experimental Pharmacology, vol. 59/2°, p. 13, "Peptides: Gastrointestinal Hormones".
The Merck Index, 10th Ed., pp. 279 and 1226.
Handbook of Experimental Pharmacology, vol. 34, p. 24.
Handbook of Experimental Pharmacology, vol. 34, p. 264, "Gastrointestinal Hormones".
Sigma Chemical Company Catalogue, pp. 277–280.

Primary Examiner—Delbert R. Phillips
Assistant Examiner—Christina Chan
Attorney, Agent, or Firm—Walter H. Schneider

[57] ABSTRACT

Pharmaceutical compositions containing a polypeptide of the cholecystokinin-cerulein group are effective in the treatment of shock conditions and of respiratory and cardiocirculatory insufficiencies.

The compositions of the invention may be administered by parenteral or inhalatory route at a dosage ranging from 5 to 20 μg of active principle per kg of body weight.

4 Claims, 1 Drawing Sheet

PHARMACEUTICAL COMPOSITIONS CONTAINING PEPTIDES OF THE CHOLECYSTOKININ-CERULEIN GROUP FOR THE THERAPY OF SHOCK CONDITIONS AND OF RESPIRATORY AND CARDIOCIRCULATORY INSUFFICIENCIES

The present invention refers to pharmaceutical compositions for the treatment of shock conditions and of respiratory and cardiocirculatory insufficiencies, comprising, as the active principle, a therapeutically effective amount of a polypeptide of the group cholecystokinin-cerulein, selected from cholecystokinin and the fragments thereof comprising the sequence 26–33 (CCK-8), gastrin and all the gastrin fragments comprising the tetrapeptide sequence L-tryptofyl-L-methionyl-L-aspartyl-L-phenylalanylamide and cerulein.

Previous therapeutic uses of said polypeptides, up to now used only as diagnostic agents, are not known. Cerulein and cholecystokinin, in fact, may be used during the performance of cholecystographies and cholangiographies and (usually in combination with secretin) in order to assay the pancreatic function. Gastrin is used to assay the stomach secretive capacity.

As it is well-known, the shock is a clinical condition essentially characterized by an insufficient tissue perfusion, with usually serious hypotension which, if not treated, is generally fatal. Shock may be caused by different causes, such as serious hemorrhages, cranial trauma, dangerous cardiac insufficiency as in certain myocardial infarcts, anaphylactic reactions, etc.

The therapy used at the present time, which is not suited for all kinds of shock, turns out to be unsatisfactory.

Generally, in all shock conditions, there is a tendency to restore the blood volume by means of blood, plasma, saline or glucose solutions or plasma substituents infusion; or to administer oxygen.

However, in serious shock conditions, said treatment is usually insufficient if not even counteracting. In fact, in the cardiogenic shock, infusion of liquids will overload the heart, whose function is already seriously impaired because of the insufficient myocardial contractility.

Administration of vasoconstrictor drugs, such as nor-adrenaline, adrenaline, metaraminol, mephentermine, in order to increase pressure, often causes the opposite effect, since, under shock conditions (with the exclusion of the neurogenic shock) a severe sympathetic reflex vasoconstriction is already present, whereby tissular perfusion would be further impaired.

On the contrary, administration of drugs such as dopamine, dobutamine, isoproterenol, glucagon, etc. which improve cardiac inotropism without substantially increasing the peripheral resistances, is preferred, particularly in case of cardiogenic shock.

On the other hand, in some instances, administration of vasodilating drugs such as nitroprussiate and α-blockers may be convenient, in order to improve tissue perfusion.

Notwithstanding corticosteroids are widely used in the treatment of shock, no convincing proofs are available supporting the effectiveness of said drugs.

Recently, the efficacy of naloxone in different models of shock has been also studied. Although naloxone turned out to be effective in restoring normal blood pressure values, it is absolutely contraindicated in the shock due to overdose. It is in fact known that naloxone administration to narcotic addicted subjects is followed by a typical abstinence syndrome.

Now it has been surprisingly found that the use of the polypeptides of the group cholecystokinin-cerulein is dramaticaly effective in the therapeutic treatment of shock (hypovolemic, cardiogenic, traumatic, toxic and anaphylactic shocks), cardiovascular collapse, acute hypotension and respiratory insufficiency, independently from the traumatic, psychogenic, toxic, drug overdose causes etc.

For instance, in the hypovolemic shock, which is always fatal when the blood loss exceeds 50% of the total blood volume, said polypeptides of the cholecystokinin-cerulein are able to restore to the normal values cardiac output, arterial pressure and breath frequency and amplitude. This effect starts to appear already a few minutes after intravenous injection, it reaches the maximum within 15–20 minutes, it is dose-dependent and require no simultaneous infusion of blood or plasma substitutes.

Even when used as analeptic, said polypeptides show, remarkable advantages in comparison with known analeptics. In fact, all the up to now available analeptics are convulsivant agents used at sub-convulsive dosages, and therefore with a very low therapeutic index and poor handling characteristics; moreover, said polypeptides normalize the circulatory and respiratory functions if they are depressed, without changing them when they are normal.

Said polypeptides are substantially non-toxic and devoid of remarkable side effects.

An object of the present invention is therefore provided by a pharmaceutical composition for the therapeutic treatment of shock conditions and of respiratory and circulatory insufficiencies, characterized by comprising:

(1) as an active principle, a therapeutically effective amount of a polypeptide of the group cholecystokinin-cerulein, selected from cholecystokinin and the fragments thereof comprising the sequence 26–33 (CCK-8), gastrin and all the gastrin fragments comprising the tetrapeptide sequence L-tryptofyl-L-methionyl-L-aspartyl-L-phenylalanylamide and cerulein; and (2) a pharmaceutically acceptable excipients.

Administration of said polypeptides will be preferably carried out by the intravenous route in the shock conditions and by nasal inhalation when the polypeptides are used as analeptics.

In any case, it has been found that the therapeutically effective dose is comprised from about 5 to about 20 μg of said polypeptides per kg body weight.

A suitable pharmaceutical composition to be administered parenterally, in form of a unit dosage, will comprise from about 0,5 to about 2 mg of said polypeptides and a pharmacologically acceptable excipient.

The above mentioned composition will be generally extemporaneously prepared by the physician or by the patient. The commercially available pharmaceutical form will be therefore a preparation in unit dosage form comprising a vial containing from about 0,5 about 2 mg of polypeptide and a vial containing a pharmaceutically acceptable solvent for said polypeptide.

When used as an analeptic for the treatment of respiratory and cardiocirculatory insufficiencies the pharmaceutical composition according to the invention will be in an appropriate form for administration by the inhalatory route, for example as a nasal spray, and it will therefore comprise a therapeutically effective amount of a polypeptide and a gaseous or vaporizable pharmaceutically acceptable excipient. The choice of the most suitable excipients is within the skilled in the art's reach.

The effectiveness of said polypeptides in the treatment of shock has been confirmed by several tests on animals and by clinical studies. Some of said tests and the obtained results are reported hereinafter.

TESTS ON EXPERIMENTAL ANIMALS

Intact and adrenalectomized female Wistar rats (Nossan, Correzzano, Milano, Italy) weighing 250 to 300 g were used. Following anesthetization and heparinization a common carotid artery and an iliac vein were cannulated in rats. Arterial blood pressure was recorded by means of a pressure transducer (Statham P23 Db) connected to a polygraph (Battaglia-Rangoni, Bologna, Italy). In some rats, trachea was cannulated and respiration was recorded by means of a transducer (Statham 10272) connected to the same polygraph. Hypovolemic shock was produced by intermittently withdrawing blood from the venous catheter until mean arterial pressure fell to 10-25 mm Hg. The volume of blood removed was 2-2.5 ml per 100 g of body weight and approximated to, or even exceeded, 50% of the estimated total blood volume. Following bleeding and mean blood pressure stabilization in the range of 10-25 mm Hg, animals were given intravenous bolus of the polypeptides. Control animals were intravenously injected with the same volume of saline (0.1 ml/100 g).

In FIGS. 1-3 some representative recordings are reported, while the Table shows the data from some tests.

From the examination of the recordings and data it is evident that the intravenous injection of polypeptides dose-dependently restores blood pressure and pulse amplitude, the effect starting within a few minutes, gradually increasing, and reaching a maximum in 15-20 minutes. All rats intravenously injected with the same volume of saline died after about 8-22 minutes.

The results from this study demonstrate that the polypeptides according to the invention increase blood pressure and reverse otherwise fatal hypovolemic shock resulting from massive bleeding.

Although it is not intended neither necessary to rely on any theoretical interpretation to explain the therapeutic effectiveness of the polypeptides in the applications of the present invention, the obtained results, showing that said polypeptides are even more active than naloxone in reversing shock, and that their action is very probably at the CNS level, are consistent with the hypothesis that melanocortins are endogenous antagonists of opioids, and give further experimental support to the suggested existence of a melanocortin-opioid peptidergic system, with a wide functional meaning and with homeostatic, regulatory roles in many, important functions of the body.

In the light of the present results, the hypothesis that shock, rather than the consequence of a massive activation of endogenous opioid system, is the final effect of the melanocortin-opioid homeostasis with prevalence of the opioid component, should be formulated.

With reference to the diagrams illustrates in the drawings.

TABLE 1

Figure 1:
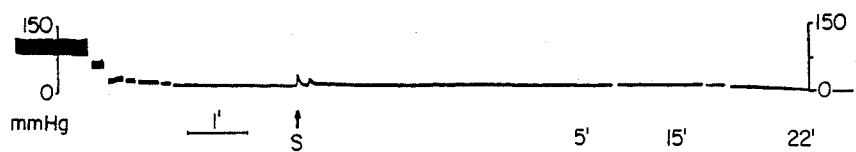
FIG. 1 shows the effect of a saline solution (s), 0.1 ml/100 g body weight, on the blood pressure after serious hypotension induced by bleeding in the intact rat.
Figure 2:
FIG. 2 shows the effect of fragment (CCK-8) of cholecystokinin, 20 μg/kg i.v. on the blood pressure after serious hypotension induced by bleeding in the adrenalectomized rat.
Figure 3:
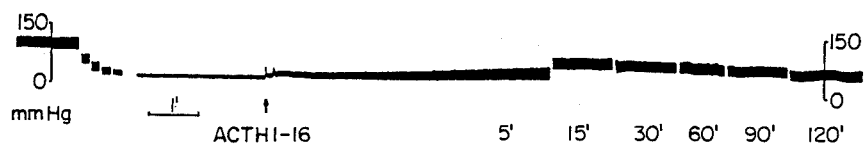
FIG. 3 shows the effect of cerulein (Ce), 20 μg/rat i.v. on the blood pressure after serious hypotension induced by bleeding in the intact rat.

Effect of saline, cholecystokinin (CCK-8) and cerulein, treatment on mean arterial pressure, respiratory rate and survival, following severe hypotension induced by bleeding

| ANIMALS* | TREATMENT AFTER BLEEDING (μg/kg i.v.) | MEAN ARTERIAL PRESSURE (mm Hg; m ± S.E.) | | | No. of deaths 120 min. after treatment |
|---|---|---|---|---|---|
| | | Before bleeding | After bleeding | 15-30 min. After bleeding | |
| Rats (12) | Physiol.sol. i.v. | 72.43 ± 8.60 | 17.50 ± 4.36** | 18.25 ± 3.91 | 12 |
| Rats (6) | CCK8, 5 | 71.17 ± 6.07 | 11.83 ± 0.79** | 26.33 ± 7.05° | 2 |
| Rats (5) | CCK8, 10 | 68.40 ± 4.98 | 14.00 ± 1.82** | 41.80 ± 3.79*** | 0 |
| Rats (5) | CCK8, 20 | 72.00 ± 4.67 | 14.40 ± 0.87** | 52.40 ± 2.73*** | 0 |
| Rats (6) | Cerulein, 20 | 75.17 ± 6.62 | 12.17 ± 1.11** | 54.67 ± 4.29*** | 0 |

*In parentheses the number of animals used;
**P < 0.02, at least, versus value before bleeding;
***P < 0.01, at least, versus value after bleeding;
°P < 0.05, at least, versus value after bleeding (Student's t-test for paired data).

I claim:

1. A method of therapeutically treating a subject suffering from shock, and respiratory and circulatory insufficiencies which comprises administering to said subject a therapeutically effective amount of a pharmaceutical composition comprising as the principal active ingredient a polypeptide selected from (a) cholecystokinin, (b) any fragment of cholecystokinin provided it comprises the sequence 26-33 (CCK-8), (c) gastrin, (d) any fragment of gastrin provide it comprises the tetrapeptidic sequence L-tryptophyl-L-methionyl-L-aspartyl-L-phenylalaninamide, (e) and cerulein, together with a pharmaceutically acceptable carrier.

2. A method according to claim 1 for treating a subject suffering from shock in which the pharmaceutical composition is in unit dosage form comprising 0.5-2 mg of said polypeptide and is administered parenterally.

3. A method according to claim 1 for treating a subject suffering from respiratory and cardiovascular insufficiencies in which the pharmaceutical composition comprises a gaseous or vaporizable carrier and is administered inhalatorally.

4. A method according to claim 2 for treating a subject suffering from shock in which the pharmaceutical composition is in the form of a kit comprising a vial of said polypeptide and a vial of a pharmaceutically acceptable solvent for said polypeptide.

* * * * *